United States Patent
de-Villiers-zur Hausen et al.

(10) Patent No.: US 6,610,303 B1
(45) Date of Patent: Aug. 26, 2003

(54) PAPILLOMA VIRUSES, PRODUCTS FOR THE DETECTION THEREOF AS WELL AS FOR TREATING DISEASES CAUSED BY THEM

(75) Inventors: Ethel-Michele de-Villiers-zur Hausen, Waldmichelbach (DE); Harald zur Hausen, Waldmichelbach (DE); Donna Lavergne, Flörsheim/Dalsheim (DE); Claire Benton, Edinburgh (GB)

(73) Assignee: Deutsches Krebsforschungszentrum Stiftung des Öffentlichen Rechts

( * ) Notice: Subject to any disclaimer, the term of this patent is extended or adjusted under 35 U.S.C. 154(b) by 0 days.

(21) Appl. No.: 09/402,016

(22) PCT Filed: Mar. 24, 1998

(86) PCT No.: PCT/DE98/00876

§ 371 (c)(1),
(2), (4) Date: Dec. 23, 1999

(87) PCT Pub. No.: WO98/42847

PCT Pub. Date: Oct. 1, 1998

(30) Foreign Application Priority Data

Mar. 25, 1997 (DE) .......................................... 197 12 541

(51) Int. Cl.[7] .................... A61K 39/12; A61K 39/42; C12N 15/37; C07K 14/025; C07K 16/08; C12Q 1/70

(52) U.S. Cl. .................... 424/204.1; 536/23.72; 435/5; 435/91.1; 435/235.1; 435/320.1; 435/252.3; 435/325; 435/69.3; 530/389.4; 530/350; 424/139.1; 424/159.1

(58) Field of Search ................ 536/23.72; 530/350, 530/389.4; 435/235.1, 320.1, 5, 91.1, 252.3, 325, 69.3; 424/204.1, 139.1, 159.1

(56) References Cited

FOREIGN PATENT DOCUMENTS

EP 0458668 A1 * 11/1991 ............ C12Q/1/70

OTHER PUBLICATIONS

Berkhout et al. Journal of Clinical Microbiology 33(3): 690–695, 1995.*
Kirnbauer et al. Journal of the National Cancer Institute 86(7): 494–499, 1994.*

* cited by examiner

*Primary Examiner*—Mary E. Mosher
(74) *Attorney, Agent, or Firm*—Pennie & Edmonds LLP

(57) ABSTRACT

This invention relates to a DNA coding for a peptide of a papilloma virus major capsid protein and a papilloma virus genome, respectively. In addition, this invention concerns proteins coded by the papilloma virus genome and antibodies directed against them as well as their use for diagnosis, treatment and vaccination.

40 Claims, 9 Drawing Sheets

FIG. 1

DL231.seq from 1 to 419:

```
         CAAGGTCACAATAATGGCATCTTATGGGGTAATCAATTGTTTGTCACTGTATTAGACAAC
    1    ---------+---------+---------+---------+---------+---------+  60
         GTTCCAGTGTTATTACCGTAGAATACCCCATTAGTTAACAAACAGTGACATAATCTGTTG

Q  G  H  N  N  G  I  L  W  G  N  Q  L  F  V  T  V  L  D  N   -

ACAAGAAATACTAACTTTAGTATAGCAGTTTATAATGATTCTGGTGAAATTAAAGACATT
   61    ---------+---------+---------+---------+---------+---------+ 120
         TGTTCTTTATGATTGAAATCATATCGTCAAATATTACTAAGACCACTTTAATTTCTGTAA

T  R  N  T  N  F  S  I  A  V  Y  N  D  S  G  E  I  K  D  I   -

GCTTCTTATGATTCCACTAAATTTCGAGAGTTTCAAAGACATGTGGAAGAATATGAGATT
  121    ---------+---------+---------+---------+---------+---------+ 180
         CGAAGAATACTAAGGTGATTTAAAGCTCTCAAAGTTTCTGTACACCTTCTTATACTCTAA

A  S  Y  D  S  T  K  F  R  E  F  Q  R  H  V  E  E  Y  E  I   -

TCTTTAATTTTACAGTTATGCAAAATTCCTTTAAAATCAGAGGTATTAGCTCAAATTAAT
  181    ---------+---------+---------+---------+---------+---------+ 240
         AGAAATTAAAATGTCAATACGTTTTAAGGAAATTTTAGTCTCCATAATCGAGTTTAATTA

S  L  I  L  Q  L  C  K  I  P  L  K  S  E  V  L  A  Q  I  N   -

GCTATGAATCCTACAATACTTGAGGATTGGCAATTAGGTTTTGTGCCAACTCCTGATAAT
  241    ---------+---------+---------+---------+---------+---------+ 300
         CGATACTTAGGATGTTATGAACTCCTAACCGTTAATCCAAAACACGGTTGAGGACTATTA

A  M  N  P  T  I  L  E  D  W  Q  L  G  F  V  P  T  P  D  N   -

CCAATACAGGATGCTTACAGATATTTGGATTCTCTGGCTACACGGTGCCCAGATAAAACT
  301    ---------+---------+---------+---------+---------+---------+ 360
         GGTTATGTCCTACGAATGTCTATAAACCTAAGAGACCGATGTGCCACGGGTCTATTTTGA

P  I  Q  D  A  Y  R  Y  L  D  S  L  A  T  R  C  P  D  K  T   -

CCAGTTAAAGAAAAAGAGGATCCATATGGGAAATATGTATTTTGGAATGTTGATCTAAC
  361    ---------+---------+---------+---------+---------+--------- 419
         GGTCAATTTCTTTTTCTCCTAGGTATACCCTTTATACATAAAACCTTACAACTAGATTG

DL250.seq from 1 to 380:

```
      AATCAGCTGTTTGTTACTGTAGCAGATAACACTAGAAATACCAACTTTACTATTAGTGTA
  1   ---------+---------+---------+---------+---------+---------+  60
      TTAGTCGACAAACAATGACATCGTCTATTGTGATCTTTATGGTTGAAATGATAATCACAT

N  Q  L  F  V  T  V  A  D  N  T  R  N  T  N  F  T  I  S  V   -

ACAACAGAAAATCCAGGGGCACAAGAATATAATGCTACTAATATAAGAGAATATTTACGA
 61   ---------+---------+---------+---------+---------+---------+ 120
      TGTTGTCTTTTAGGTCCCCGTGTTCTTATATTACGATGATTATATTCTCTTATAAATGCT

T  T  E  N  P  G  A  Q  E  Y  N  A  T  N  I  R  E  Y  L  R   -

CATGTAGAGGAGTATCAAATATCATTAATCTTACAATTGTGCAAGGTTCCCTTAACTTCA
121   ---------+---------+---------+---------+---------+---------+ 180
      GTACATCTCCTCATAGTTTATAGTAATTAGAATGTTAACACGTTCCAAGGGAATTGAAGT

H  V  E  E  Y  Q  I  S  L  I  L  Q  L  C  K  V  P  L  T  S   -

GAAGTACTATCACAAATTAATGCCATGAACTCTGGTATTTTAGAAGAATGGCAACTAGGG
181   ---------+---------+---------+---------+---------+---------+ 240
      CTTCATGATAGTGTTTAATTACGGTACTTGAGACCATAAAATCTTCTTACCGTTGATCCC

E  V  L  S  Q  I  N  A  M  N  S  G  I  L  E  E  W  Q  L  G   -

TTTGTGCCAACCCCAGACAATGCTGTTCATGATATGTATAGATATATTAATTCTAAAGCA
241   ---------+---------+---------+---------+---------+---------+ 300
      AAACACGGTTGGGGTCTGTTACGACAAGTACTATACATATCTATATAATTAAGATTTCGT

F  V  P  T  P  D  N  A  V  H  D  M  Y  R  Y  I  N  S  K  A   -

ACTAAATGTCCTGATGCTGTAGAACCTACAGAAAGAGAGGATCCATTTGCTAAATATACT
301   ---------+---------+---------+---------+---------+---------+ 360
      TGATTTACAGGACTACGACATCTTGGATGTCTTTCTCTCCTAGGTAAACGATTTATATGA

T  K  C  P  D  A  V  E  P  T  E  R  E  D  P  F  A  K  Y  T   -

TTTTGGAATGTTGATCTAAC
361   ---------+---------+ 380
      AAAACCTTACAACTAGATTG

DL253.seq from 1 to 458:

```
     CAAGGTCACAATAATGGTATACTATGGGGAAATCAAATGTTTGTCACTGTTGCTGATAAC
1    ---------+---------+---------+---------+---------+---------+ 60
     GTTCCAGTGTTATTACCATATGATACCCCTTTAGTTTACAAACAGTGACAACGACTATTG

Q  G  H  N  N  G  I  L  W  G  N  Q  M  F  V  T  V  A  D  N   -

ACTAGAAACACTAACTTTACCATTTGTGTACCTTCAGATAATGGTGCTATAACTGAGTAT
61   ---------+---------+---------+---------+---------+---------+ 120
     TGATCTTTGTGATTGAAATGGTAAACACATGGAAGTCTATTACCACGATATTGACTCATA

T  R  N  T  N  F  T  I  C  V  P  S  D  N  G  A  I  T  E  Y   -

GATTCTAGCAAATTTAGAGAATTTTTAAGGCACGTGGAAGAGTATCAAATATCTGTAATA
121  ---------+---------+---------+---------+---------+---------+ 180
     CTAAGATCGTTTAAATCTCTTAAAAATTCCGTGCACCTTCTCATAGTTTATAGACATTAT

D  S  S  K  F  R  E  F  L  R  H  V  E  E  Y  Q  I  S  V  I   -

TTACAACTGTGTAAAGTATCACTGCAACCTGATGTGCTAGCCCAGATCAATGCAATGAAT
181  ---------+---------+---------+---------+---------+---------+ 240
     AATGTTGACACATTTCATAGTGACGTTGGACTACACGATCGGGTCTAGTTACGTTACTTA

L  Q  L  C  K  V  S  L  Q  P  D  V  L  A  Q  I  N  A  M  N   -

TCAGGTATATTAGAAGATTGGCAGTTAGGATTTGTACCAACTCCTGACAATGCAGTACAT
241  ---------+---------+---------+---------+---------+---------+ 300
     AGTCCATATAATCTTCTAACCGTCAATCCTAAACATGGTTGAGGACTGTTACGTCATGTA

S  G  I  L  E  D  W  Q  L  G  F  V  P  T  P  D  N  A  V  H   -

GACACCTATAGATTTATAAATTCCTCAGCCACTAAATGTCCAGATAAGGTTCCTGCTAAA
301  ---------+---------+---------+---------+---------+---------+ 360
     CTGTGGATATCTAAATATTTAAGGAGTCGGTGATTTACAGGTCTATTCCAAGGACGATTT

D  T  Y  R  F  I  N  S  S  A  T  K  C  P  D  K  V  P  A  K   -

GATAGAGAGGATCCATTTGCTCAATATTTCTTTTGGAGAGTAGATATGACTGAAAAATTA
361  ---------+---------+---------+---------+---------+---------+ 420
     CTATCTCTCCTAGGTAAACGAGTTATAAAGAAAACCTCTCATCTATACTGACTTTTTAAT

D  R  E  D  P  F  A  Q  Y  F  F  W  R  V  D  M  T  E  K  L   -

TCATTAGATTTAGACCAATATCCTTTGGGACGAAAATT
421  ---------+---------+---------+-------- 458
     AGTAATCTAAATCTGGTTATAGGAAACCCTGCTTTTAA

DL267.seq from 1 to 380:

```
      AATCAACTGTTTATTACTGTAGCAGACAACACCCGTAATACTAATTTTACAATCAGTGTT
  1   ---------+---------+---------+---------+---------+---------+  60
      TTAGTTGACAAATAATGACATCGTCTGTTGTGGGCATTATGATTAAAATGTTAGTCACAA

N  Q  L  F  I  T  V  A  D  N  T  R  N  T  N  F  T  I  S  V  -

ACTAGTGAAGACTTAAGTACAGCAAAATATGATGCTAAAAATATCAGGGAATATATGAGA
 61   ---------+---------+---------+---------+---------+---------+ 120
      TGATCACTTCTGAATTCATGTCGTTTTATACTACGATTTTTATAGTCCCTTATATACTCT

T  S  E  D  L  S  T  A  K  Y  D  A  K  N  I  R  E  Y  M  R  -

CATGTAGAAGAATATCAATTATCATTTATATTACAGTTATGTAGGGTACCCTTAGAGGCT
121   ---------+---------+---------+---------+---------+---------+ 180
      GTACATCTTCTTATAGTTAATAGTAAATATAATGTCAATACATCCCATGGGAATCTCCGA

H  V  E  E  Y  Q  L  S  F  I  L  Q  L  C  R  V  P  L  E  A  -

GAGGTGCTAACCCAGATTAATGCTATGAATTCAGGTATATTAGAAAACTGGCAACTAGGG
181   ---------+---------+---------+---------+---------+---------+ 240
      CTCCACGATTGGGTCTAATTACGATACTTAAGTCCATATAATCTTTTGACCGTTGATCCC

E  V  L  T  Q  I  N  A  M  N  S  G  I  L  E  N  W  Q  L  G  -

TTTGTTCCAACACCAGATAATGCAGTGCATGACACATATCGTTACCTTAATTCAAAAGCT
241   ---------+---------+---------+---------+---------+---------+ 300
      AAACAAGGTTGTGGTCTATTACGTCACGTACTGTGTATAGCAATGGAATTAAGTTTTCGA

F  V  P  T  P  D  N  A  V  H  D  T  Y  R  Y  L  N  S  K  A  -

ACAAAATGTCCAGATGCAGTTCGAGAAACAGAAAAGGAAGATCCTTTTGGTGGATATTCA
301   ---------+---------+---------+---------+---------+---------+ 360
      TGTTTTACAGGTCTACGTCAAGCTCTTTGTCTTTTCCTTCTAGGAAAACCACCTATAAGT

T  K  C  P  D  A  V  R  E  T  E  K  E  D  P  F  G  G  Y  S  -

TTCTGGAATGTTGATCTAAC
361   ---------+---------+ 380
      AAGACCTTACAACTAGATTG

DL284.seq from 1 to 389:

```
     AATCAACTGTTTGTTACTGTATTAGATAATACTAGAAATACAAACTTTAGTATTGCTGTT
  1  ---------+---------+---------+---------+---------+---------+ 60
     TTAGTTGACAAACAATGACATAATCTATTATGATCTTTATGTTTGAAATCATAACGACAA

N  Q  L  F  V  T  V  L  D  N  T  R  N  T  N  F  S  I  A  V  -

TATCAAGAGCAGAAGCAGGTTAAAGAAATACAAAATTATGATTCTGCAAAGTTTAATGAA
 61  ---------+---------+---------+---------+---------+---------+ 120
     ATAGTTCTCGTCTTCGTCCAATTTCTTTATGTTTTAATACTAAGACGTTTCAAATTACTT

Y  Q  E  Q  K  Q  V  K  E  I  Q  N  Y  D  S  A  K  F  N  E  -

TTTCAGAGACATGTTGAAGAATATGAAGTTTCTCTCATTTTACAATTGTGTAAAATTCCA
121  ---------+---------+---------+---------+---------+---------+ 180
     AAAGTCTCTGTACAACTTCTTATACTTCAAAGAGAGTAAAATGTTAACACATTTTAAGGT

F  Q  R  H  V  E  E  Y  E  V  S  L  I  L  Q  L  C  K  I  P  -

TTGAAAGCTGAGGTTCTTGCACAGATTAATGCAATGAACTCCGATATTTTAGAAAATTGG
181  ---------+---------+---------+---------+---------+---------+ 240
     AACTTTCGACTCCAAGAACGTGTCTAATTACGTTACTTGAGGCTATAAAATCTTTTAACC

L  K  A  E  V  L  A  Q  I  N  A  M  N  S  D  I  L  E  N  W  -

CAGTTAGGTTTTGTACCTACGCCAGACAATCCTATTCATGATACCTACAGATATTTAGAC
241  ---------+---------+---------+---------+---------+---------+ 300
     GTCAATCCAAAACATGGATGCGGTCTGTTAGGATAAGTACTATGGATGTCTATAAATCTG

Q  L  G  F  V  P  T  P  D  N  P  I  H  D  T  Y  R  Y  L  D  -

TCATTAGCAACACGCTGTCCAGAAAAAGTTCCAGCAAAGGAAAACGTAGACCCTTATGCT
301  ---------+---------+---------+---------+---------+---------+ 360
     AGTAATCGTTGTGCGACAGGTCTTTTTCAAGGTCGTTTCCTTTTGCATCTGGGAATACGA

S  L  A  T  R  C  P  E  K  V  P  A  K  E  N  V  D  P  Y  A  -

AAGTATGTATTTTGGGATGTTGATCTATC
361  ---------+---------+--------- 389
     TTCATACATAAAACCCTACAACTAGATAG

DL285.seq from 1 to 458:

```
         CAGGGTCATAATAATGGCATCCTATGGGGAAACCAAATGTTTGTTACTGTTGCAGACAAT
      1  ---------+---------+---------+---------+---------+---------+  60
         GTCCCAGTATTATTACCGTAGGATACCCCTTTGGTTTACAAACAATGACAACGTCTGTTA

Q  G  H  N  N  G  I  L  W  G  N  Q  M  F  V  T  V  A  D  N   -

ACAAGGAACACCAATTTTACTATAAGTGTGCCTAGTCAAAATGGACCCCTTACAGAATAT
     61  ---------+---------+---------+---------+---------+---------+  120
         TGTTCCTTGTGGTTAAAATGATATTCACACGGATCAGTTTTACCTGGGGAATGTCTTATA

T  R  N  T  N  F  T  I  S  V  P  S  Q  N  G  P  L  T  E  Y   -

GATGCCAATAATATCAGGGAATTTTTAAGGCATGTTGAGGAATATCAAATATCTGTAATA
    121  ---------+---------+---------+---------+---------+---------+  180
         CTACGGTTATTATAGTCCCTTAAAAATTCCGTACAACTCCTTATAGTTTATAGACATTAT

D  A  N  N  I  R  E  F  L  R  H  V  E  E  Y  Q  I  S  V  I   -

CTACAACTTTGTAAAGTGTCTTTACAACCAGATGTATTAGCCCAAATTAATGCTATGAAT
    181  ---------+---------+---------+---------+---------+---------+  240
         GATGTTGAAACATTTCACAGAAATGTTGGTCTACATAATCGGGTTTAATTACGATACTTA

L  Q  L  C  K  V  S  L  Q  P  D  V  L  A  Q  I  N  A  M  N   -

TCAGGCATTTTGGAAGACTGGCAATTAGGTTTTGTACCAACACCAGATAATTCAGTTCAT
    241  ---------+---------+---------+---------+---------+---------+  300
         AGTCCGTAAAACCTTCTGACCGTTAATCCAAAACATGGTTGTGGTCTATTAAGTCAAGTA

S  G  I  L  E  D  W  Q  L  G  F  V  P  T  P  D  N  S  V  H   -

GACACTTATAGATTTATTAATTCTACTGCTACTAAATGTCCTGACAAGGTTGCTCCTAAA
    301  ---------+---------+---------+---------+---------+---------+  360
         CTGTGAATATCTAAATAATTAAGATGACGATGATTTACAGGACTGTTCCAACGAGGATTT

D  T  Y  R  F  I  N  S  T  A  T  K  C  P  D  K  V  A  P  K   -

GAAAAGGAAGATCCTTTTGCTCAATACTTTTTCTGGAGAGTTGATATGACAGAAAAATTA
    361  ---------+---------+---------+---------+---------+---------+  420
         CTTTTCCTTCTAGGAAAACGAGTTATGAAAAAGACCTCTCAACTATACTGTCTTTTTAAT

E  K  E  D  P  F  A  Q  Y  F  F  W  R  V  D  M  T  E  K  L   -

TCTTTGGATTTAGACCAATATCCTCTGGGACGAAAATT
    421  ---------+---------+---------+--------  458
         AGAAACCTAAATCTGGTTATAGGAGACCCTGCTTTTAA

DL287.seq from 1 to 467:

```
    CAGGGTCACAACAATGGCATCTTATGGGGTAATCAATTGTTTGTGACTGTATTAGATAAC
  1 ---------+---------+---------+---------+---------+---------+  60
    GTCCCAGTGTTGTTACCGTAGAATACCCCATTAGTTAACAAACACTGACATAATCTATTG

Q  G  H  N  N  G  I  L  W  G  N  Q  L  F  V  T  V  L  D  N   -

ACTAGAAACACCAACTTTAGTATTGCTGTTTATCAAGAACAGAAAAAGGTGAAAGAAATA
 61 ---------+---------+---------+---------+---------+---------+ 120
    TGATCTTTGTGGTTGAAATCATAACGACAAATAGTTCTTGTCTTTTTCCACTTTCTTTAT

T  R  N  T  N  F  S  I  A  V  Y  Q  E  Q  K  K  V  K  E  I   -

CAGAGTTACGATTCTACCAAGTTTAATGAATTCCAAAGACATGTGGAAGAATATGAAGTA
121 ---------+---------+---------+---------+---------+---------+ 180
    GTCTCAATGCTAAGATGGTTCAAATTACTTAAGGTTTCTGTACACCTTCTTATACTTCAT

Q  S  Y  D  S  T  K  F  N  E  F  Q  R  H  V  E  E  Y  E  V   -

TCACTTATTCTACAGCTTTGTAAAATTCCACTAAAAGCTGAGGTGCTAGCACAGATTAAT
181 ---------+---------+---------+---------+---------+---------+ 240
    AGTGAATAAGATGTCGAAACATTTTAAGGTGATTTTCGACTCCACGATCGTGTCTAATTA

S  L  I  L  Q  L  C  K  I  P  L  K  A  E  V  L  A  Q  I  N   -

GCAATGAACTCTGACATTTTGGAAAGTTGGCAGTTAGGTTTTGTACCTACACCAGATAAT
241 ---------+---------+---------+---------+---------+---------+ 300
    CGTTACTTGAGACTGTAAAACCTTTCAACCGTCAATCCAAAACATGGATGTGGTCTATTA

A  M  N  S  D  I  L  E  S  W  Q  L  G  F  V  P  T  P  D  N   -

CCTATCCACGACACATACAGATACTTAGATTCATTGGCTACCCGCTGCCCAGAAAAAGTG
301 ---------+---------+---------+---------+---------+---------+ 360
    GGATAGGTGCTGTGTATGTCTATGAATCTAAGTAACCGATGGGCGACGGGTCTTTTTCAC

P  I  H  D  T  Y  R  Y  L  D  S  L  A  T  R  C  P  E  K  V   -

CCTGCAAAGGAAAAGGAGGACCCTTATGCTAAGTATGTATTTTGGAATGTTGATTTGTCT
361 ---------+---------+---------+---------+---------+---------+ 420
    GGACGTTTCCTTTTCCTCCTGGGAATACGATTCATACATAAAACCTTACAACTAAACAGA

P  A  K  E  K  E  D  P  Y  A  K  Y  V  F  W  N  V  D  L  S   -

GAACGTTTATCTTTGGATTTGGACCAATTTCCTTTAGGACGAAAATT
421 ---------+---------+---------+---------+------- 467
    CTTGCAAATAGAAACCTAAACCTGGTTAAAGGAAATCCTGCTTTTAA

DL297.seq from 1 to 467:

```
     CAAGGTCACAATAATGGTATTCTGTGGGCTAATGAAATGTTTGTCACTGTTGTAGACAAC
  1  ---------+---------+---------+---------+---------+---------+  60
     GTTCCAGTGTTATTACCATAAGACACCCGATTACTTTACAAACAGTGACAACATCTGTTG

Q   G   H   N   N   G   I   L   W   A   N   E   M   F   V   T   V   V   D   N   -

ACACGAAATACTAATTTCAGTATATCCATGTATACAGAAGCTGGGGAGATAAAAAATATA
 61  ---------+---------+---------+---------+---------+---------+ 120
     TGTGCTTTATGATTAAAGTCATATAGGTACATATGTCTTCGACCCCTCTATTTTTTATAT

T   R   N   T   N   F   S   I   S   M   Y   T   E   A   G   E   I   K   N   I   -

GCCAACTACGATGCCAAAAAATTTAGGGAGTATTTAAGACACGTGGAAGAGTATGAAATT
121  ---------+---------+---------+---------+---------+---------+ 180
     CGGTTGATGCTACGGTTTTTTAAATCCCTCATAAATTCTGTGCACCTTCTCATACTTTAA

A   N   Y   D   A   K   K   F   R   E   Y   L   R   H   V   E   E   Y   E   I   -

TCTCTAATTTCACAACTTTGTAAAATACCTCTGAAGGCAGAGGTCCTTGCACAAATAAAT
181  ---------+---------+---------+---------+---------+---------+ 240
     AGAGATTAAAGTGTTGAAACATTTTATGGAGACTTCCGTCTCCAGGAACGTGTTTATTTA

S   L   I   S   Q   L   C   K   I   P   L   K   A   E   V   L   A   Q   I   N   -

GCAATGAATTCCTCTTTATTGGAGGACTGGCAACTGGGGTTTGTGCCTACCCCTGATAAT
241  ---------+---------+---------+---------+---------+---------+ 300
     CGTTACTTAAGGAGAAATAACCTCCTGACCGTTGACCCCAAACACGGATGGGGACTATTA

A   M   N   S   S   L   L   E   D   W   Q   L   G   F   V   P   T   P   D   N   -

CCCATACAAGACACTTATAGATATATTGATTCCTTAGCCACACGTTGTCCTGACAAAAAT
301  ---------+---------+---------+---------+---------+---------+ 360
     GGGTATGTTCTGTGAATATCTATATAACTAAGGAATCGGTGTGCAACAGGACTGTTTTTA

P   I   Q   D   T   Y   R   Y   I   D   S   L   A   T   R   C   P   D   K   N   -

CCTCCAAAGGAAAAAGAAGATCCCTATAAAAAATTTAACTTTTTGGACTGTAGATCTTACT
361  ---------+---------+---------+---------+---------+---------+ 420
     GGAGGTTTCCTTTTTCTTCTAGGGATATTTTTAAATTGAAAAACCTGACATCTAGAATGA

P   P   K   E   K   E   D   P   Y   K   N   L   T   F   W   T   V   D   L   T   -

GAGCGACTTTCCTTGGAGTTGGATCAATATCCTCTGGGACGAAAGTT
421  ---------+---------+---------+---------+------- 467
     CTCGCTGAAAGGAACCTCAACCTAGTTATAGGAGACCCTGCTTTCAA

DL332.seq from 1 to 389:

```
    AATCAAATGTTTATTACAGTGGTAGACAACACACGAAACACCAATTTCAGTATTTCAGTT
  1 ---------+---------+---------+---------+---------+---------+  60
    TTAGTTTACAAATAATGTCACCATCTGTTGTGTGCTTTGTGGTTAAAGTCATAAAGTCAA

N  Q  M  F  I  T  V  V  D  N  T  R  N  T  N  F  S  I  S  V  -

TATAGTGAAGGTGGACAAATAAAAGATATCAGGGACTACACATCTACACAGTTCAGGGAA
 61 ---------+---------+---------+---------+---------+---------+  120
    ATATCACTTCCACCTGTTTATTTTCTATAGTCCCTGATGTGTAGATGTGTCAAGTCCCTT

Y  S  E  G  G  Q  I  K  D  I  R  D  Y  T  S  T  Q  F  R  E  -

TATTTAAGGCATGTGGAGGAATATGAAATATCTGTCATATTGCAGTTATGTAAAATACCT
121 ---------+---------+---------+---------+---------+---------+  180
    ATAAATTCCGTACACCTCCTTATACTTTATAGACAGTATAACGTCAATACATTTTATGGA

Y  L  R  H  V  E  E  Y  E  I  S  V  I  L  Q  L  C  K  I  P  -

TTAAAAGCAGAAGTCTTGGCTCAAATAAATGCCATGAACCCCTTATTATTGGAGGACTGG
181 ---------+---------+---------+---------+---------+---------+  240
    AATTTTCGTCTTCAGAACCGAGTTTATTTACGGTACTTGGGGAATAATAACCTCCTGACC

L  K  A  E  V  L  A  Q  I  N  A  M  N  P  L  L  L  E  D  W  -

CAATTAGGATTTGTCCCTACACCTGACAATCCAATTCATGATACCTACAGATTTATTGAC
241 ---------+---------+---------+---------+---------+---------+  300
    GTTAATCCTAAACAGGGATGTGGACTGTTAGGTTAAGTACTATGGATGTCTAAATAACTG

Q  L  G  F  V  P  T  P  D  N  P  I  H  D  T  Y  R  F  I  D  -

TCTTTGGCTATCCGATGCCCTGACAAAAATCCCCCAAAAGAAAAACCTGACCCTTATGAA
301 ---------+---------+---------+---------+---------+---------+  360
    AGAAACCGATAGGCTACGGGACTGTTTTTAGGGGGTTTTCTTTTTGGACTGGGAATACTT

S  L  A  I  R  C  P  D  K  N  P  P  K  E  K  P  D  P  Y  E  -

GGCTTAAACTTTTGGAATGTTGATCTATC
361 ---------+---------+---------  389
    CCGAATTTGAAAACCTTACAACTAGATAG

G  L  N  F  W  N  V  D  L     -
```

PAPILLOMA VIRUSES, PRODUCTS FOR THE DETECTION THEREOF AS WELL AS FOR TREATING DISEASES CAUSED BY THEM

TABLE OF CONTENTS

I. FIELD OF THE INVENTION
II. BACKGROUND OF THE INVENTION
III. SUMMARY OF THE INVENTION
IV. BRIEF DESCRIPTION OF THE DRAWINGS
V. DETAILED DESCRIPTION OF THE INVENTION
VI. EXAMPLES
   A. Example 1: Identification of the Papilloma Virus Genome D1231-g
   B. Example 2: Cloning of the Papilloma Virus Genome D1231 -g This is a national phase filing of the Application No. PCT/DE/00876, which was filed with the Patent Corporation Treaty on Mar. 24, 1998, and is entitled to priority of the German Patent Application 197 12 541, filed Mar. 25, 1997.

I. FIELD OF THE INVENTION

This invention relates to a DNA coding for a peptide of a papilloma virus major capsid protein and a papilloma virus genome, respectively. In addition, this invention concerns proteins coded by the papilloma virus genome and antibodies directed against them as well as their use for diagnosis, treatment and vaccination.

II. BACKGROUND OF THE INVENTION

It is known that papilloma viruses infect the epithelium of human beings and animals. Human papilloma viruses (hereinafter referred to as HP viruses) are found in benign epithelial neoplasms, e.g. warts, condylomas in the genital zone, and malignant epithelial neoplasms, e.g. carcinomas of the skin and the uterus (Zur Hausen, H., 1996, *Biochimica et Biophsica Acta* (*BBA*) 1288:55–78). HP viruses are also considered for the growth of malignant tumors in the oropharyngeal zone (Zur Hausen, H., 1977, *Curr. Top. Microbiol. Immunol.* 78:1–30).

Papilloma viruses have an icosahedral capsid without envelope in which a circular, double-stranded DNA molecule of about 7900 bp is present. The capsid comprises a major capsid protein (L1) and a minor capsid protein (L2). Both proteins, coexpressed or L1 expressed alone, result in vitro in the formation of virus-like particles (Kirnbauer, R. et al., 1993, *Journal of Virology* 67:6929–6936).

Papilloma viruses cannot be proliferated in monolayer cell culture. Therefore, their characterization is extremely difficult, the detection of papilloma viruses already creating considerable problems. This applies particularly to papilloma viruses in carcinomas of the skin.

Thus, it is the object of the present invention to provide a product by which papilloma viruses can be detected, particularly in carcinomas of the skin. Furthermore, a product should be provided to be able to take therapeutic steps against these papilloma viruses.

III. SUMMARY OF THE INVENTION

This invention relates to a DNA coding for a peptide of a papilloma virus major capsid protein and a papilloma virus genome, respectively. In addition, this invention concerns proteins coded by the papilloma virus genome and antibodies directed against them as well as their use for diagnosis, treatment and vaccination.

IV. BRIEF DESCRIPTION OF THE DRAWINGS

FIG. 1 (SEQ ID NO: 1) shows the base sequence and the amino acid sequence (SEQ ID NO: 2), derived therefrom, of a DNA coding for a peptide of L1 of a papilloma virus. This DNA was deposited as plasmid DL231 with DSM (*Deutsche Sammlung von Mikroogranismen und Zellkulturen* [German-type collection of micro-organisms and cell cultures]) under DSM 11405 on Feb. 13, 1997.

FIG. 2 shows the base sequence (SEQ ID NO: 3) and the amino acid sequence (SEQ ID NO: 4), derived therefrom, of a DNA coding for a peptide of L1 of a papilloma virus. This DNA was deposited as plasmid KL250 with DSM under DSM 11406 on Feb. 13, 1997.

FIG. 3 shows the base sequence (SEQ ID NO: 5) and the amino acid sequence (SEQ ID NO: 6), derived therefrom, of a DNA coding for a peptide of L1 of a papilloma virus. This DNA was deposited as plasmid DL253 with DSM under DSM 11407 on Feb. 13, 1997.

FIG. 4 shows the base sequence (SEQ ID NO: 7) and the amino acid sequence (SEQ ID NO: 8), derived therefrom, of a DNA coding for a peptide of L1 of a papilloma virus. This DNA was deposited as plasmid DL267 with DSM under DSM 11408 on Feb. 13, 1997.

FIG. 5 shows the base sequence (SEQ ID NO: 9) and the amino acid sequence (SEQ ID NO: 10), derived therefrom, of a DNA coding for a peptide of L1 of a papilloma virus. This DNA was deposited as plasmid DL284 with DSM under DSM 11409 on Feb. 13, 1997.

FIG. 6 shows the base sequence (SEQ ID NO: 11) and the amino acid sequence (SEQ ID NO: 12), derived therefrom, of a DNA coding for a peptide of L1 of a papilloma virus. This DNA was deposited as plasmid DL285 with DSM under DSM 11410 on Feb. 13, 1997.

FIG. 7 shows the base sequence (SEQ ID NO: 13) and the amino acid sequence (SEQ ID NO: 14), derived therefrom, of a DNA coding for a peptide of L1 of a papilloma virus. This DNA was deposited as plasmid DL287 with DSM under DSM 11411 on Feb. 13, 1997.

FIG. 8 shows the base sequence (SEQ ID NO: 15) and the amino acid sequence (SEQ ID NO: 16), derived therefrom, of a DNA coding for a peptide of L1 of a papilloma virus. This DNA was deposited as plasmid DL297 with DSM under DSM 11412 on Feb. 13, 1997.

FIG. 9 shows the base sequence (SEQ ID NO: 17) and the amino acid sequence (SEQ ID NO: 18), derived therefrom, of a DNA coding for a peptide of L1 of a papilloma virus. This DNA was deposited as plasmid DL332 with DSM under DSM 11413 on Feb. 13, 1997.

V. DETAILED DESCRIPTION OF THE INVENTION

It is the object of the present invention to provide a product by which papilloma viruses can be detected, particularly in carcinomas of the skin. Furthermore, a product should be provided to be able to take therapeutic steps against these papilloma viruses.

According to the invention this is achieved by providing the subject matters in the claims.

Therefore, the subject matter of the invention relates to a DNA coding for a peptide of a papilloma virus major capsid protein (L1), the peptide comprising the amino acid sequence of FIG. 1 (SEQ ID NO: 2), FIG. 2 (SEQ ID NO: 4), FIG. 3 (SEQ ID NO: 6), FIG. 4 (SEQ ID NO: 8), FIG. 5 (SEQ ID NO: 10), FIG. 6 (SEQ ID NO: 12), FIG. 7 (SEQ ID NO: 14), FIG. 8 (SEQ ID NO: 16), FIG. 9 (SEQ ID NO: 18) or an amino acid sequence differing therefrom by one or more amino acids.

A further subject matter of the invention relates to a DNA coding for a peptide of a papilloma virus major capsid protein, the DNA comprising the base sequence of FIG. 1 (SEQ ID NO: 1), FIG. 2 (SEQ ID NO: 3), FIG. 3 (SEQ ID NO: 5), FIG. 4 (SEQ ID NO: 7), FIG. 5 (SEQ ID NO: 9), FIG. 6 (SEQ ID NO: 11), FIG. 7 (SEQ ID NO: 13), FIG. 8 (SEQ ID NO: 15), or FIG. 9 (SEQ ID NO: 17) or a base sequence differing therefrom by one or more base pairs.

The above DNA was compared with the DNA of known papilloma viruses. Sequence homology studies were carried out. A homology having less than 90% shows that a DNA according to the invention is a new HP virus. The DNAs according to the invention have the following sequence homologies with respect to known papilloma viruses:

DNA of FIG. 1 (SEQ ID NO: 1): 77% with respect to HP virus 5c

DNA of FIG. 2 (SEQ ID NO: 3): 80% with respect to HP virus 9

DNA of FIG. 3 (SEQ ID NO: 5): 76% with respect to HP virus 38

DNA of FIG. 4 (SEQ ID NO: 7): 79% with respect to HP virus 38

DNA of FIG. 5 (SEQ ID NO: 9): 74% with respect to HP virus 20

DNA of FIG. 6 (SEQ ID NO: 11): 77% with respect to HP virus 9

DNA of FIG. 7 (SEQ ID NO: 13): 73% with respect to HP virus 20

DNA of FIG. 8 (SEQ ID NO: 15): 87% with respect to HP virus 5b

DNA of FIG. 9 (SEQ ID NO: 17): 78% with respect to HP virus 5b.

According to the invention, the above DNA can be present in a vector and expression vector, respectively. A person skilled in the art is familiar with examples thereof. In the case of an expression vector for *E. coli* these are e.g. pGEMEX, pUC derivatives, pGEM-T and pGEX-2T. For the expression in yeast e.g. pY100 and Ycpad1 have to be mentioned, while for the expression in animal cells e.g. pKCR, pEF-BOS, cDM8 and pCEV4 have to be indicated.

The person skilled in the art knows suitable cells to express the above DNA present in an expression vector. Examples of such cells comprise the *E. coli* strains HB101, DH1, x1776, JM101, JM109, and XL1-Blue, the yeast strain *Saccharomyces cerevisiae* and the animal cells L, NH-3T3, FM3A, CHO, COS, Vero, and HeLa.

The person skilled in the art knows in which way the above DNA has to be inserted in an expression vector. He is also familiar with the fact that the above DNA can be inserted in connection with a DNA coding for another protein and peptide, respectively, so that the above DNA can be expressed in the from of a fusion protein.

A further subject matter of the invention relates to a papilloma virus genome which comprises the above DNA. The expression "papilloma virus genome" also comprises an incomplete genome, i.e. fragments of a papilloma virus genome, which comprise the above DNA. This may be e.g a DNA coding for L1 or a portion thereof.

A common process can be used for the provision of the above papilloma virus genome. It is favorable to use a process which comprises the following processing steps:
(a) isolation of the total DNA from a biopsy of epithelial neoplasm,
(b) hybridization of the total DNA of (a) with the above DNA so as to detect a papilloma virus genome included in the total DNA of (a), and
(c) cloning of the total DNA of (a), containing the papilloma virus genome, in a vector and optionally subcloning the resulting clone, all processing steps originating from common DNA recombination technique.

As far as the isolation, hybridization and cloning of cell DNA is concerned, reference is made by way of supplement to Sambrook et al., Molecular Cloning, A Laboratory Manual, second edition, Cold Spring Harbor Laboratory (1989).

The expression "epithelial neoplasm" comprises any neoplasms of epithelium in man and animal. Examples of such neoplasms are warts, condylomas in the genital zone and carcinomas of the skin. The latter are used preferably to isolate the above papilloma virus genome.

The expression "vector" comprises any vectors suitable for cloning chromosomal DNA and extrachromosomal DNA, respectively. Examples of such vectors are cosmids such as pWE15 and Super Cos 1, and phages such as λ-phages, e.g. λ-ZAP expression vector, λ-ZAPII vector and λgt10 vector. In the present case, λ-phages are used preferably. The above vectors are known and obtainable from the company of Stratagene.

Papilloma virus genomes according to the invention may be present in integrated form in chromosomal DNA or in extrachromosomal fashion. The person skilled in the art is familiar with processes serving the clarification thereof. He also knows processes serving for finding out the optimum restriction enzymes for cloning the papilloma virus genomes. He will orient himself by genomes of known papilloma viruses. In particular, the person skilled in the art will pay corresponding attention to the above-mentioned HP viruses.

The provision of a papilloma virus genome referred to as DL231-G is described by way of example. For this purpose, the total DNA is isolated from a biopsy of a squamous epithelial carcinoma, cleaved by BamHI and separated electrophoretically in an agarose gel. The agarose gel is then subjected to a blotting method so as to transfer the DNA to a nitrocellulose membrane. It is inserted in a bybridization method in which the DNA of FIG. 1 (SEQ ID NO: 1) is used as labeled sample, optionally in combination with a DNA of HP virus 5c. Hybridization with the papilloma virus DNA present in the total DNA is obtained.

Moreover, the above, total DNA cleaved by BamHI is cloned in a λ-phage. The corresponding clones, i.e. the clones containing the papilloma virus DNA are identified by hybridizaiton with the DNA of FIG. 1 (SEQ ID NO: 1), optionally in combination with a DNA of the HP virus 5c. The insert of these clones is then subjected to a further cloning in a plasmid vector so as to obtain a clone which contains the papilloma virus genome DL231-G. The genome is confirmed by sequencing.

Further papilloma virus genomes are provided analogously. They are designated in accordance with the DNAs used for their provision, namely by: DL250-G, DL253-G, DL267-G, DL284-G, DL285-G, DL287-G, DL297-G and DL332-G, respectively.

A further subject matter of the invention relates to a protein which is coded by the above papilloma virus genome. Such a protein is e.g. a major capsid protein (L1) or a minor capsid protein (L2). An above protein is prepared as usual. The preparation of L1 and L2, respectively, of the papilloma virus genome DL231-G is described by way of example. For this purpose, the HP virus 5c related to the DNA of FIG. 1 (SEQ ID NO: 1) is used. Its full sequence and the position of individual DNA regions coding for proteins are known. These DNAs are identified on the papilloma virus genome DL231-G by parallel restriction cleavages of both genomes and subsequent hybridization with various fragments concerning the DNA encoding L1 and L2, respectively. They are confirmed by sequencing. The DNA coding for L1 is referred to as DL231-G-L1 DNA and the DNA coding for L2 is referred to as DL231-G-L2 DNA.

Furthermore, the DNA coding for L1 and L2, respectively, is inserted in an expression vector. Examples thereof are mentioned above for *E. coli*, yeast and animal cells. In particular, reference is made to the vector pGEX-2T as regards the expression in *E. coli* (Kirnbauer, R. et al., supra). Having inserted the DL231-G-L1 DNA and DL231-G-L2 DNA, one obtains pGEX-2T-DL231-L1 and pGEX-2T-DL231-G-L2, respectively. After transforming *E. coli*, these expression vectors express a glutathione S transferase L1 fusion protein and glutathione S transferase L2 fusion protein, respectively. The proteins are purified as usual.

The baculovirus system and vaccinia virus system, respectively, is mentioned for a further expression of the above DNA encoding L1 and L2, respectively. Expression vectors usable for this purpose are e.g. pEV mod. and pSynwtVI⁻for the bacculovirus system (Kirnbauer, R. et al., supra). For the vaccinia virus system especially vectors with the vaccinia virus "early" (p7.5 k) promoter and "late" (Psynth, p11K promoter, respectively, have to be mentioned (Hagensee, M., E. et al., 1993, *Journal of Virology* 67:315–322). The bacculovirus system is preferred in the present case. Having inserted the above DNA encoding L1 and L2, respectively, in pEV mod., one obtains pEVmod.-DL231-G-L1 and pEVmod.-DL231-G-L2, respectively.

The former expression vector as such or both expression vectors jointly lead to the formation of virus-like particles after infection of SF-9 insect cells. In the former case, such a particle comprises an L1 protein, while in the latter case it contains an L2 protein in addition to an L1 protein.

A virus-like particle of the latter case is also obtained by inserting the above DL231-G-L1 and DL231-G-L2 DNAs jointly in the expression vector pSynwtVI⁻and using the resulting pSynwtVI⁻DL231-G-L1/L2 for the infection of SF-9 insect cells. The above virus-like particles are purified as usual. They also represent a subject matter of the invention.

A further subject matter of the invention relates to an antibody directed against an above protein and virus-like particle, respectively. The preparation thereof is made as usual. It is described by way of example for the preparation of an antibody which is directed against a virus-like particle comprising an L1 of DL231-G. For this purpose, the virus-like particle is injected subcutaneously into BALB/c mice. This injection is repeated at intervals of 3 weeks each. About 2 weeks after the last injection, the serum containing the antibody is isolated and tested as usual.

In a preferred embodiment, the antibody is a monoclonal antibody. For its preparation, spleen cells are removed from the mice after the above, fourth injection and fused with myeloma cells as usual. The further cloning also takes place according to known methods.

By means of the present invention it is possible to detect papilloma viruses, particularly in carcinomas of the skin. For this purpose, the DNA according to the invention can be used as such or when comprised by a further DNA. The latter may also be a papilloma virus genome or a portion thereof.

The present invention also enables the provision of formerly unknown papilloma viruses. They are found especially in carcinomas of the skin. In addition, the invention supplies proteins and virus-like particles which originate from these papilloma viruses. Moreover, antibodies are provided which are directed against these proteins and particles, respectively.

The present invention also enables to take diagnostic and therapeutic steps in the case of papilloma virus diseases. Moreover, it supplies the possibility of building up a vaccine against papilloma virus infections. Thus, the present invention represents a break-through in the field of papilloma virus research.

The invention is explained by the examples.

VI. EXAMPLES

A. Example 1

Identification of the Papilloma Virus Genome D1231-g

The total DNA is isolated from a biopsy of Verruca vulgaris. 10 μg of this DNA are cleaved by the restriction enzyme BamHI and separated electrophoretically in a 0.5% agarose gel. At the same time, 10 μg of the above DNA which was not cleaved is also separated. The agarose gel is subjected to a blotting method so as to transfer the DNA from the agarose gel to a nitrocellulose membrane. It is employed in a hybridization method in which the above DNA of FIG. 1 (SEQ ID NO: 1) is used in combination with the HP virus-5c DNA as $P^{32}$-labeled sample. Hybridization with the blotted DNA is obtained.

The person skilled in the field of DNA recombination technique is familiar with the above methods. Reference is made to Sambrook et al., supra by way of supplement.

B. Example 2

Cloning of the Papilloma Virus Genome D1231-g

The biopsy DNA obtained from Example 1 is cleaved by the restriction enzyme BamHI. The resulting fragments are used in a ligase reaction in which the dephosphorylated vector λ-ZAP express cleaved by BamHI is also present. The resulting recombinant DNA molecules are packed in bacteriophages, and they are used for infecting bacteria. For these processing steps, the ZAP expression vector kit offered by the company of Stratagene is used. The resulting phage plaques are then subjected to a hybridization process which uses the $P^{32}$-labeled DNA of FIG. 1 (SEQ ID NO: 1) employed in Example 1 in combination with $P^{32}$-labeled HP virus-5c DNA. Hybridization with corresponding phage plaques is obtained. The BamHI fragments of DL231-G are isolated therefrom and used in a further ligase reaction together with a BamHI-cleaved, dephosphorylated plasmid vector, pBluescript. The resulting recombinant DNA molecules are used for transforming bacteria, *E. coli* XL1-Blue. By restriction cleavages and hybridization with the above DNA samples, respectively, a bacterial clone containing the papilloma virus genome DL231-G is identified. The plasmid of this bacterial clone is referred to as pBlue-DL231-G.

What is claimed is:

1. An isolated polynucleotide encoding a peptide of a papilloma virus major capsid protein, said polynucleotide consisting essentially of:
   (a) the nucleotide sequence of SEQ ID NO:1;
   (b) a nucleotide sequence hybridizing to the nucleotide sequence of SEQ ID NO:1; or
   (c) the complement of (a) or (b);
   wherein the polynucleotide has a homology of at least 90% to the entire length of the nucleotide sequence of SEQ ID NO:1, or the complement thereof.

2. An isolated polynucleotide encoding a peptide of a papilloma virus major capsid protein, wherein the said polynucleotide has been obtained using the following steps:
   (a) incubating total DNA isolated from a biopsy of epithelial neoplasm with a nucleic acid having at least a portion of the nucleotide sequence of SEQ ID NO:1, under a condition that allows hybridization of a polynucleotide derived from a papilloma virus genome included in the total DNA to said nucleotide sequence of the complement of SEQ ID NO:1; and
   (b) identifying and isolating a polynucleotide that hybridizes to the complement of nucleotide sequence of SEQ ID NO:1 or the complement thereof in step (a);
   wherein the polynucleotide has a homology of at least 90% to the entire length of the nucleotide sequence of SEQ ID NO:1.

3. The isolated polynucleotide of claim 1 or 2, wherein said polynucleotide encodes a peptide comprising the amino acid sequence of SEQ ID NO:2.

4. The isolated polynucleotide of claim 1 or 2, wherein the polynucleotide consists essentially of the nucleotide sequence of SEQ ID NO:1.

5. A polypeptide encoded by the polynucleotide of claim 1 or 2.

6. A polypeptide encoded by the polynucleotide of claim 3.

7. A virus-like particle comprising the polypeptide of claim 5.

8. The virus-like particle of claim 7, further comprising a papilloma virus minor capsid protein.

9. A virus-like particle comprising the polypeptide of claim 6.

10. The virus-like particle of claim 9, further comprising a papilloma virus minor capsid protein.

11. An expression vector comprising a polynucleotide encoding a peptide of a papilloma virus major capsid protein, said polynucleotide consisting essentially of:

(a) the nucleotide sequence of SEQ ID NO:1;

(b) a nucleotide sequence hybridizing to the nucleotide sequence of SEQ ID NO:1; or (c) the complement of (a) or (b);

wherein the polynucleotide has a homology of at least 90% to the entire length of the nucleotide sequence of SEQ ID NO:1, or the complement thereof.

12. An expression vector comprising a polynucleotide encoding a peptide comprising the amino acid sequence of SEQ ID NO:2.

13. A host cell comprising the expression vector of claim 11.

14. A host cell comprising the expression vector of claim 12.

15. A method of producing a peptide of a papilloma virus major capsid protein, comprising cultivating the host cell of claim 13 under suitable conditions.

16. A method of producing a peptide of a papilloma virus major capsid protein, comprising cultivating the host cell of claim 14 under suitable conditions.

17. An antibody that immunospecifically binds the polypeptide of claim 5.

18. An antibody that immunospecifically binds the polypeptide of claim 6.

19. A method of detecting a papilloma virus DNA, comprising:

(a) hybridizing under stringent conditions at least a portion of a polynucleotide encoding a peptide of a papilloma virus major capsid protein to a DNA sample, wherein said polynucleotide encoding a peptide of a papilloma virus major capsid protein consists essentially of (i) the nucleotide sequence of SEQ ID NO:1; (ii) a nucleotide sequence hybridizing to the nucleotide sequence of SEQ ID NO:1; or (iii) the complement of (i) or (ii);

wherein the polynucleotide has a homology of at least 90% to the entire length of the nucleotide sequence of SEQ ID NO:1, or the complement thereof; and (b) identifying papilloma virus in said DNA sample by detecting a hybridization signal.

20. A composition comprising the polypeptide of claim 5.

21. A composition comprising the polypeptide of claim 6.

22. A composition comprising the virus-like particle of claim 7.

23. A composition comprising the virus-like particle of claim 8.

24. A composition comprising the virus-like particle of claim 9.

25. A composition comprising the virus-like particle of claim 10.

26. A composition comprising the antibody of claim 17.

27. A composition comprising the antibody of claim 18.

28. A composition comprising the polynucleotide of claim 1 or 2 and a diagnostically acceptable carrier.

29. A pharmaceutical composition comprising the virus-like particle according to claim 7, and a pharmaceutically acceptable carrier.

30. A pharmaceutical composition comprising the virus-like particle according to claim 8, and a pharmaceutically acceptable carrier.

31. A pharmaceutical composition comprising the virus-like particle according to claim 9, and a pharmaceutically acceptable carrier.

32. A pharmaceutical composition comprising the virus-like particle according to claim 10; and a pharmaceutically acceptable carrier.

33. A pharmaceutical composition comprising the antibody of claim 17, and a pharmaceutically acceptable carrier.

34. A pharmaceutical composition comprising the antibody of claim 18, and a pharmaceutically acceptable carrier.

35. A method of producing a papilloma virus genome, comprising:

(a) incubating total DNA isolated from a biopsy of epithelial neoplasm with a nucleic acid having at least a portion of the nucleotide sequence of SEQ ID NO:1, under a condition that allows hybridization of a polynucleotide derived from a papilloma virus genome included in the total DNA to said nucleotide sequence of the complement of SEQ ID NO:1; and (b) identifying and isolating a polynucleotide that hybridizes to the nucleotide sequence of the complement of SEQ ID NO:1 in step (a);

wherein a portion of the polynucleotide has a homology of at least 90% to the entire length of the nucleotide sequence of SEQ ID NO:1, or the complement thereof.

36. A method of diagnosing a papilloma virus in a patient sample, comprising:

(a) incubating the patient sample with the antibody of claim 17; and (b) identifying immunospecific binding of the antibody to papilloma virus in said patient sample.

37. A method of treating a papilloma virus infection in a patient in need, comprising administering to said patient the pharmaceutical composition of claim 33.

38. A method of vaccinating a subject in need against papilloma virus, comprising administering to said subject the composition of claim 20.

39. A method of vaccinating a subject in need against papilloma virus, comprising administering to said subject the composition of claim 22.

40. An expression vector comprising a polynucleotide encoding a peptide of a papilloma virus major capsid protein, wherein the said polynucleotide has been obtained using the following steps:

(a) incubating total DNA isolated from a biopsy of epithelial neoplasm with a nucleic acid having at least a portion of the nucleotide sequence of SEQ ID NO:1, under a condition that allows hybridization of a polynucleotide derived from a papilloma virus genome included in the total DNA to said nucleotide sequence of the complement of SEQ ID NO:1; and (b) identifying and isolating a polynucleotide that hybridizes to the complement of nucleotide sequence of SEQ ID NO:1 or the complement thereof in step (a);

wherein the polynucleotide has a homology of at least 90% to the nucleotide sequence of SEQ ID NO:1.

* * * * *

SEQUENCE LISTING

<160> NUMBER OF SEQ ID NOS: 18

<210> SEQ ID NO 1
<211> LENGTH: 419
<212> TYPE: DNA
<213> ORGANISM: Papilloma virus capsid
<220> FEATURE:
<221> NAME/KEY: CDS
<222> LOCATION: (1)..(417)
<223> OTHER INFORMATION:

<400> SEQUENCE: 1

```
caa ggt cac aat aat ggc atc tta tgg ggt aat caa ttg ttt gtc act        48
Gln Gly His Asn Asn Gly Ile Leu Trp Gly Asn Gln Leu Phe Val Thr
  1               5                  10                  15 gta tta gac aac aca aga aat act aac ttt agt ata gca gtt tat aat        96
Val Leu Asp Asn Thr Arg Asn Thr Asn Phe Ser Ile Ala Val Tyr Asn
             20                  25                  30 gat tct ggt gaa att aaa gac att gct tct tat gat tcc act aaa ttt       144
Asp Ser Gly Glu Ile Lys Asp Ile Ala Ser Tyr Asp Ser Thr Lys Phe
         35                  40                  45 cga gag ttt caa aga cat gtg gaa gaa tat gag att tct tta att tta       192
Arg Glu Phe Gln Arg His Val Glu Glu Tyr Glu Ile Ser Leu Ile Leu
     50                  55                  60 cag tta tgc aaa att cct tta aaa tca gag gta tta gct caa att aat       240
Gln Leu Cys Lys Ile Pro Leu Lys Ser Glu Val Leu Ala Gln Ile Asn
 65                  70                  75                  80 gct atg aat cct aca ata ctt gag gat tgg caa tta ggt ttt gtg cca       288
Ala Met Asn Pro Thr Ile Leu Glu Asp Trp Gln Leu Gly Phe Val Pro
                 85                  90                  95 act cct gat aat cca ata cag gat gct tac aga tat ttg gat tct ctg       336
Thr Pro Asp Asn Pro Ile Gln Asp Ala Tyr Arg Tyr Leu Asp Ser Leu
            100                 105                 110 gct aca cgg tgc cca gat aaa act cca gtt aaa gaa aaa gag gat cca       384
Ala Thr Arg Cys Pro Asp Lys Thr Pro Val Lys Glu Lys Glu Asp Pro
        115                 120                 125 tat ggg aaa tat gta ttt tgg aat gtt gat cta ac                        419
Tyr Gly Lys Tyr Val Phe Trp Asn Val Asp Leu
    130                 135
```

<210> SEQ ID NO 2
<211> LENGTH: 139
<212> TYPE: PRT
<213> ORGANISM: Papilloma virus capsid

<400> SEQUENCE: 2

```
Gln Gly His Asn Asn Gly Ile Leu Trp Gly Asn Gln Leu Phe Val Thr
  1               5                  10                  15

Val Leu Asp Asn Thr Arg Asn Thr Asn Phe Ser Ile Ala Val Tyr Asn
             20                  25                  30

Asp Ser Gly Glu Ile Lys Asp Ile Ala Ser Tyr Asp Ser Thr Lys Phe
         35                  40                  45

Arg Glu Phe Gln Arg His Val Glu Glu Tyr Glu Ile Ser Leu Ile Leu
     50                  55                  60

Gln Leu Cys Lys Ile Pro Leu Lys Ser Glu Val Leu Ala Gln Ile Asn
 65                  70                  75                  80

Ala Met Asn Pro Thr Ile Leu Glu Asp Trp Gln Leu Gly Phe Val Pro
                 85                  90                  95

Thr Pro Asp Asn Pro Ile Gln Asp Ala Tyr Arg Tyr Leu Asp Ser Leu
```

| | | | 100 | | | | 105 | | | | 110 | | |
|---|---|---|---|---|---|---|---|---|---|---|---|---|---|
Ala Thr Arg Cys Pro Asp Lys Thr Pro Val Lys Glu Lys Glu Asp Pro
           115                 120                 125

Tyr Gly Lys Tyr Val Phe Trp Asn Val Asp Leu
    130               135

<210> SEQ ID NO 3
<211> LENGTH: 380
<212> TYPE: DNA
<213> ORGANISM: Papilloma virus capsid
<220> FEATURE:
<221> NAME/KEY: CDS
<222> LOCATION: (1)..(378)
<223> OTHER INFORMATION:

<400> SEQUENCE: 3

| | | | | | | | | | | | | | | | | |
|---|---|---|---|---|---|---|---|---|---|---|---|---|---|---|---|---|
| aat | cag | ctg | ttt | gtt | act | gta | gca | gat | aac | act | aga | aat | acc | aac | ttt | 48 |
| Asn | Gln | Leu | Phe | Val | Thr | Val | Ala | Asp | Asn | Thr | Arg | Asn | Thr | Asn | Phe | |
| 1 | | | | 5 | | | | | 10 | | | | | 15 | | |

| act | att | agt | gta | aca | aca | gaa | aat | cca | ggg | gca | caa | gaa | tat | aat | gct | 96 |
|---|---|---|---|---|---|---|---|---|---|---|---|---|---|---|---|---|
| Thr | Ile | Ser | Val | Thr | Thr | Glu | Asn | Pro | Gly | Ala | Gln | Glu | Tyr | Asn | Ala | |
| | | | 20 | | | | | 25 | | | | | 30 | | | |

| act | aat | ata | aga | gaa | tat | tta | cga | cat | gta | gag | gag | tat | caa | ata | tca | 144 |
|---|---|---|---|---|---|---|---|---|---|---|---|---|---|---|---|---|
| Thr | Asn | Ile | Arg | Glu | Tyr | Leu | Arg | His | Val | Glu | Glu | Tyr | Gln | Ile | Ser | |
| | | 35 | | | | | 40 | | | | | 45 | | | | |

| tta | atc | tta | caa | ttg | tgc | aag | gtt | ccc | tta | act | tca | gaa | gta | cta | tca | 192 |
|---|---|---|---|---|---|---|---|---|---|---|---|---|---|---|---|---|
| Leu | Ile | Leu | Gln | Leu | Cys | Lys | Val | Pro | Leu | Thr | Ser | Glu | Val | Leu | Ser | |
| 50 | | | | | 55 | | | | | 60 | | | | | | |

| caa | att | aat | gcc | atg | aac | tct | ggt | att | tta | gaa | gaa | tgg | caa | cta | ggg | 240 |
|---|---|---|---|---|---|---|---|---|---|---|---|---|---|---|---|---|
| Gln | Ile | Asn | Ala | Met | Asn | Ser | Gly | Ile | Leu | Glu | Glu | Trp | Gln | Leu | Gly | |
| 65 | | | | 70 | | | | | 75 | | | | | 80 | | |

| ttt | gtg | cca | acc | cca | gac | aat | gct | gtt | cat | gat | atg | tat | aga | tat | att | 288 |
|---|---|---|---|---|---|---|---|---|---|---|---|---|---|---|---|---|
| Phe | Val | Pro | Thr | Pro | Asp | Asn | Ala | Val | His | Asp | Met | Tyr | Arg | Tyr | Ile | |
| | | | | 85 | | | | | 90 | | | | | 95 | | |

| aat | tct | aaa | gca | act | aaa | tgt | cct | gat | gct | gta | gaa | cct | aca | gaa | aga | 336 |
|---|---|---|---|---|---|---|---|---|---|---|---|---|---|---|---|---|
| Asn | Ser | Lys | Ala | Thr | Lys | Cys | Pro | Asp | Ala | Val | Glu | Pro | Thr | Glu | Arg | |
| | | | | 100 | | | | | 105 | | | | | 110 | | |

| gag | gat | cca | ttt | gct | aaa | tat | act | ttt | tgg | aat | gtt | gat | cta | ac | | 380 |
|---|---|---|---|---|---|---|---|---|---|---|---|---|---|---|---|---|
| Glu | Asp | Pro | Phe | Ala | Lys | Tyr | Thr | Phe | Trp | Asn | Val | Asp | Leu | | | |
| | | | 115 | | | | | 120 | | | | | 125 | | | |

<210> SEQ ID NO 4
<211> LENGTH: 126
<212> TYPE: PRT
<213> ORGANISM: Papilloma virus capsid

<400> SEQUENCE: 4

Asn Gln Leu Phe Val Thr Val Ala Asp Asn Thr Arg Asn Thr Asn Phe
1               5                 10              15

Thr Ile Ser Val Thr Thr Glu Asn Pro Gly Ala Gln Glu Tyr Asn Ala
           20                 25               30

Thr Asn Ile Arg Glu Tyr Leu Arg His Val Glu Glu Tyr Gln Ile Ser
               35                40              45

Leu Ile Leu Gln Leu Cys Lys Val Pro Leu Thr Ser Glu Val Leu Ser
   50                55                60

Gln Ile Asn Ala Met Asn Ser Gly Ile Leu Glu Glu Trp Gln Leu Gly
65                 70                75              80

Phe Val Pro Thr Pro Asp Asn Ala Val His Asp Met Tyr Arg Tyr Ile
               85                90              95

Asn Ser Lys Ala Thr Lys Cys Pro Asp Ala Val Glu Pro Thr Glu Arg

-continued

```
                    100                 105                 110
Glu Asp Pro Phe Ala Lys Tyr Thr Phe Trp Asn Val Asp Leu
            115                 120                 125

<210> SEQ ID NO 5
<211> LENGTH: 458
<212> TYPE: DNA
<213> ORGANISM: Papilloma virus capsid
<220> FEATURE:
<221> NAME/KEY: CDS
<222> LOCATION: (1)..(456)
<223> OTHER INFORMATION:

<400> SEQUENCE: 5 caa ggt cac aat aat ggt ata cta tgg gga aat caa atg ttt gtc act      48
Gln Gly His Asn Asn Gly Ile Leu Trp Gly Asn Gln Met Phe Val Thr
1               5                   10                  15 gtt gct gat aac act aga aac act aac ttt acc att tgt gta cct tca      96
Val Ala Asp Asn Thr Arg Asn Thr Asn Phe Thr Ile Cys Val Pro Ser
            20                  25                  30 gat aat ggt gct ata act gag tat gat tct agc aaa ttt aga gaa ttt     144
Asp Asn Gly Ala Ile Thr Glu Tyr Asp Ser Ser Lys Phe Arg Glu Phe
        35                  40                  45 tta agg cac gtg gaa gag tat caa ata tct gta ata tta caa ctg tgt     192
Leu Arg His Val Glu Glu Tyr Gln Ile Ser Val Ile Leu Gln Leu Cys
    50                  55                  60 aaa gta tca ctg caa cct gat gtg cta gcc cag atc aat gca atg aat     240
Lys Val Ser Leu Gln Pro Asp Val Leu Ala Gln Ile Asn Ala Met Asn
65                  70                  75                  80 tca ggt ata tta gaa gat tgg cag tta gga ttt gta cca act cct gac     288
Ser Gly Ile Leu Glu Asp Trp Gln Leu Gly Phe Val Pro Thr Pro Asp
                85                  90                  95 aat gca gta cat gac acc tat aga ttt ata aat tcc tca gcc act aaa     336
Asn Ala Val His Asp Thr Tyr Arg Phe Ile Asn Ser Ser Ala Thr Lys
            100                 105                 110 tgt cca gat aag gtt cct gct aaa gat aga gag gat cca ttt gct caa     384
Cys Pro Asp Lys Val Pro Ala Lys Asp Arg Glu Asp Pro Phe Ala Gln
        115                 120                 125 tat ttc ttt tgg aga gta gat atg act gaa aaa tta tca tta gat tta     432
Tyr Phe Phe Trp Arg Val Asp Met Thr Glu Lys Leu Ser Leu Asp Leu
    130                 135                 140 gac caa tat cct ttg gga cga aaa tt                                  458
Asp Gln Tyr Pro Leu Gly Arg Lys
145                 150

<210> SEQ ID NO 6
<211> LENGTH: 152
<212> TYPE: PRT
<213> ORGANISM: Papilloma virus capsid

<400> SEQUENCE: 6

Gln Gly His Asn Asn Gly Ile Leu Trp Gly Asn Gln Met Phe Val Thr
1               5                   10                  15

Val Ala Asp Asn Thr Arg Asn Thr Asn Phe Thr Ile Cys Val Pro Ser
            20                  25                  30

Asp Asn Gly Ala Ile Thr Glu Tyr Asp Ser Ser Lys Phe Arg Glu Phe
        35                  40                  45

Leu Arg His Val Glu Glu Tyr Gln Ile Ser Val Ile Leu Gln Leu Cys
    50                  55                  60

Lys Val Ser Leu Gln Pro Asp Val Leu Ala Gln Ile Asn Ala Met Asn
65                  70                  75                  80
```

```
Ser Gly Ile Leu Glu Asp Trp Gln Leu Gly Phe Val Pro Thr Pro Asp
                85                  90                  95

Asn Ala Val His Asp Thr Tyr Arg Phe Ile Asn Ser Ser Ala Thr Lys
            100                 105                 110

Cys Pro Asp Lys Val Pro Ala Lys Asp Arg Glu Asp Pro Phe Ala Gln
            115                 120                 125

Tyr Phe Phe Trp Arg Val Asp Met Thr Glu Lys Leu Ser Leu Asp Leu
            130                 135                 140

Asp Gln Tyr Pro Leu Gly Arg Lys
145                 150

<210> SEQ ID NO 7
<211> LENGTH: 380
<212> TYPE: DNA
<213> ORGANISM: Papilloma virus capsid
<220> FEATURE:
<221> NAME/KEY: CDS
<222> LOCATION: (1)..(378)
<223> OTHER INFORMATION:

<400> SEQUENCE: 7 aat caa ctg ttt att act gta gca gac aac acc cgt aat act aat ttt        48
Asn Gln Leu Phe Ile Thr Val Ala Asp Asn Thr Arg Asn Thr Asn Phe
1               5                   10                  15 aca atc agt gtt act agt gaa gac tta agt aca gca aaa tat gat gct        96
Thr Ile Ser Val Thr Ser Glu Asp Leu Ser Thr Ala Lys Tyr Asp Ala
            20                  25                  30 aaa aat atc agg gaa tat atg aga cat gta gaa gaa tat caa tta tca       144
Lys Asn Ile Arg Glu Tyr Met Arg His Val Glu Glu Tyr Gln Leu Ser
        35                  40                  45 ttt ata tta cag tta tgt agg gta ccc tta gag gct gag gtg cta acc       192
Phe Ile Leu Gln Leu Cys Arg Val Pro Leu Glu Ala Glu Val Leu Thr
    50                  55                  60 cag att aat gct atg aat tca ggt ata tta gaa aac tgg caa cta ggg       240
Gln Ile Asn Ala Met Asn Ser Gly Ile Leu Glu Asn Trp Gln Leu Gly
65                  70                  75                  80 ttt gtt cca aca cca gat aat gca gtg cat gac aca tat cgt tac ctt       288
Phe Val Pro Thr Pro Asp Asn Ala Val His Asp Thr Tyr Arg Tyr Leu
                85                  90                  95 aat tca aaa gct aca aaa tgt cca gat gca gtt cga gaa aca gaa aag       336
Asn Ser Lys Ala Thr Lys Cys Pro Asp Ala Val Arg Glu Thr Glu Lys
            100                 105                 110 gaa gat cct ttt ggt gga tat tca ttc tgg aat gtt gat cta ac            380
Glu Asp Pro Phe Gly Gly Tyr Ser Phe Trp Asn Val Asp Leu
        115                 120                 125

<210> SEQ ID NO 8
<211> LENGTH: 126
<212> TYPE: PRT
<213> ORGANISM: Papilloma virus capsid

<400> SEQUENCE: 8

Asn Gln Leu Phe Ile Thr Val Ala Asp Asn Thr Arg Asn Thr Asn Phe
1               5                   10                  15

Thr Ile Ser Val Thr Ser Glu Asp Leu Ser Thr Ala Lys Tyr Asp Ala
            20                  25                  30

Lys Asn Ile Arg Glu Tyr Met Arg His Val Glu Glu Tyr Gln Leu Ser
        35                  40                  45

Phe Ile Leu Gln Leu Cys Arg Val Pro Leu Glu Ala Glu Val Leu Thr
    50                  55                  60
```

Gln Ile Asn Ala Met Asn Ser Gly Ile Leu Glu Asn Trp Gln Leu Gly
65                  70                  75                  80

Phe Val Pro Thr Pro Asp Asn Ala Val His Asp Thr Tyr Arg Tyr Leu
                85                  90                  95

Asn Ser Lys Ala Thr Lys Cys Pro Asp Ala Val Arg Glu Thr Glu Lys
            100                 105                 110

Glu Asp Pro Phe Gly Gly Tyr Ser Phe Trp Asn Val Asp Leu
        115                 120                 125

<210> SEQ ID NO 9
<211> LENGTH: 389
<212> TYPE: DNA
<213> ORGANISM: Papilloma virus capsid
<220> FEATURE:
<221> NAME/KEY: CDS
<222> LOCATION: (1)..(387)
<223> OTHER INFORMATION:

<400> SEQUENCE: 9

| aat caa ctg ttt gtt act gta tta gat aat act aga aat aca aac ttt | 48 |
| Asn Gln Leu Phe Val Thr Val Leu Asp Asn Thr Arg Asn Thr Asn Phe | |
| 1               5                   10                  15 | |

| agt att gct gtt tat caa gag cag aag cag gtt aaa gaa ata caa aat | 96 |
| Ser Ile Ala Val Tyr Gln Glu Gln Lys Gln Val Lys Glu Ile Gln Asn | |
|             20                  25                  30 | |

| tat gat tct gca aag ttt aat gaa ttt cag aga cat gtt gaa gaa tat | 144 |
| Tyr Asp Ser Ala Lys Phe Asn Glu Phe Gln Arg His Val Glu Glu Tyr | |
|         35                  40                  45 | |

| gaa gtt tct ctc att tta caa ttg tgt aaa att cca ttg aaa gct gag | 192 |
| Glu Val Ser Leu Ile Leu Gln Leu Cys Lys Ile Pro Leu Lys Ala Glu | |
|     50                  55                  60 | |

| gtt ctt gca cag att aat gca atg aac tcc gat att tta gaa aat tgg | 240 |
| Val Leu Ala Gln Ile Asn Ala Met Asn Ser Asp Ile Leu Glu Asn Trp | |
| 65                  70                  75                  80 | |

| cag tta ggt ttt gta cct acg cca gac aat cct att cat gat acc tac | 288 |
| Gln Leu Gly Phe Val Pro Thr Pro Asp Asn Pro Ile His Asp Thr Tyr | |
|                 85                  90                  95 | |

| aga tat tta gac tca tta gca aca cgc tgt cca gaa aaa gtt cca gca | 336 |
| Arg Tyr Leu Asp Ser Leu Ala Thr Arg Cys Pro Glu Lys Val Pro Ala | |
|             100                 105                 110 | |

| aag gaa aac gta gac cct tat gct aag tat gta ttt tgg gat gtt gat | 384 |
| Lys Glu Asn Val Asp Pro Tyr Ala Lys Tyr Val Phe Trp Asp Val Asp | |
|         115                 120                 125 | |

| cta tc | 389 |
| Leu | |

<210> SEQ ID NO 10
<211> LENGTH: 129
<212> TYPE: PRT
<213> ORGANISM: Papilloma virus capsid

<400> SEQUENCE: 10

Asn Gln Leu Phe Val Thr Val Leu Asp Asn Thr Arg Asn Thr Asn Phe
1               5                   10                  15

Ser Ile Ala Val Tyr Gln Glu Gln Lys Gln Val Lys Glu Ile Gln Asn
            20                  25                  30

Tyr Asp Ser Ala Lys Phe Asn Glu Phe Gln Arg His Val Glu Glu Tyr
        35                  40                  45

Glu Val Ser Leu Ile Leu Gln Leu Cys Lys Ile Pro Leu Lys Ala Glu
    50                  55                  60

```
Val Leu Ala Gln Ile Asn Ala Met Asn Ser Asp Ile Leu Glu Asn Trp
 65                  70                  75                  80

Gln Leu Gly Phe Val Pro Thr Pro Asp Asn Pro Ile His Asp Thr Tyr
                 85                  90                  95

Arg Tyr Leu Asp Ser Leu Ala Thr Arg Cys Pro Glu Lys Val Pro Ala
            100                 105                 110

Lys Glu Asn Val Asp Pro Tyr Ala Lys Tyr Val Phe Trp Asp Val Asp
        115                 120                 125

Leu

<210> SEQ ID NO 11
<211> LENGTH: 458
<212> TYPE: DNA
<213> ORGANISM: Papilloma virus capsid
<220> FEATURE:
<221> NAME/KEY: CDS
<222> LOCATION: (1)..(456)
<223> OTHER INFORMATION:

<400> SEQUENCE: 11 cag ggt cat aat aat ggc atc cta tgg gga aac caa atg ttt gtt act      48
Gln Gly His Asn Asn Gly Ile Leu Trp Gly Asn Gln Met Phe Val Thr
 1               5                  10                  15 gtt gca gac aat aca agg aac acc aat ttt act ata agt gtg cct agt      96
Val Ala Asp Asn Thr Arg Asn Thr Asn Phe Thr Ile Ser Val Pro Ser
             20                  25                  30 caa aat gga ccc ctt aca gaa tat gat gcc aat aat atc agg gaa ttt     144
Gln Asn Gly Pro Leu Thr Glu Tyr Asp Ala Asn Asn Ile Arg Glu Phe
         35                  40                  45 tta agg cat gtt gag gaa tat caa ata tct gta ata cta caa ctt tgt     192
Leu Arg His Val Glu Glu Tyr Gln Ile Ser Val Ile Leu Gln Leu Cys
     50                  55                  60 aaa gtg tct tta caa cca gat gta tta gcc caa att aat gct atg aat     240
Lys Val Ser Leu Gln Pro Asp Val Leu Ala Gln Ile Asn Ala Met Asn
 65                  70                  75                  80 tca ggc att ttg gaa gac tgg caa tta ggt ttt gta cca aca cca gat     288
Ser Gly Ile Leu Glu Asp Trp Gln Leu Gly Phe Val Pro Thr Pro Asp
                 85                  90                  95 aat tca gtt cat gac act tat aga ttt att aat tct act gct act aaa     336
Asn Ser Val His Asp Thr Tyr Arg Phe Ile Asn Ser Thr Ala Thr Lys
            100                 105                 110 tgt cct gac aag gtt gct cct aaa gaa aag gaa gat cct ttt gct caa     384
Cys Pro Asp Lys Val Ala Pro Lys Glu Lys Glu Asp Pro Phe Ala Gln
        115                 120                 125 tac ttt ttc tgg aga gtt gat atg aca gaa aaa tta tct ttg gat tta     432
Tyr Phe Phe Trp Arg Val Asp Met Thr Glu Lys Leu Ser Leu Asp Leu
    130                 135                 140 gac caa tat cct ctg gga cga aaa tt                                  458
Asp Gln Tyr Pro Leu Gly Arg Lys
145                 150

<210> SEQ ID NO 12
<211> LENGTH: 152
<212> TYPE: PRT
<213> ORGANISM: Papilloma virus capsid

<400> SEQUENCE: 12

Gln Gly His Asn Asn Gly Ile Leu Trp Gly Asn Gln Met Phe Val Thr
 1               5                  10                  15

Val Ala Asp Asn Thr Arg Asn Thr Asn Phe Thr Ile Ser Val Pro Ser
```

```
                    20                  25                  30
Gln Asn Gly Pro Leu Thr Glu Tyr Asp Ala Asn Asn Ile Arg Glu Phe
         35                  40                  45

Leu Arg His Val Glu Glu Tyr Gln Ile Ser Val Ile Leu Gln Leu Cys
     50                  55                  60

Lys Val Ser Leu Gln Pro Asp Val Leu Ala Gln Ile Asn Ala Met Asn
 65                  70                  75                  80

Ser Gly Ile Leu Glu Asp Trp Gln Leu Gly Phe Val Pro Thr Pro Asp
                 85                  90                  95

Asn Ser Val His Asp Thr Tyr Arg Phe Ile Asn Ser Thr Ala Thr Lys
             100                 105                 110

Cys Pro Asp Lys Val Ala Pro Lys Glu Lys Asp Pro Phe Ala Gln
         115                 120                 125

Tyr Phe Phe Trp Arg Val Asp Met Thr Glu Lys Leu Ser Leu Asp Leu
     130                 135                 140

Asp Gln Tyr Pro Leu Gly Arg Lys
145                 150

<210> SEQ ID NO 13
<211> LENGTH: 467
<212> TYPE: DNA
<213> ORGANISM: Papilloma virus capsid
<220> FEATURE:
<221> NAME/KEY: CDS
<222> LOCATION: (1)..(465)
<223> OTHER INFORMATION:

<400> SEQUENCE: 13 cag ggt cac aac aat ggc atc tta tgg ggt aat caa ttg ttt gtg act    48
Gln Gly His Asn Asn Gly Ile Leu Trp Gly Asn Gln Leu Phe Val Thr
 1               5                  10                  15 gta tta gat aac act aga aac acc aac ttt agt att gct gtt tat caa    96
Val Leu Asp Asn Thr Arg Asn Thr Asn Phe Ser Ile Ala Val Tyr Gln
                 20                  25                  30 gaa cag aaa aag gtg aaa gaa ata cag agt tac gat tct acc aag ttt   144
Glu Gln Lys Lys Val Lys Glu Ile Gln Ser Tyr Asp Ser Thr Lys Phe
             35                  40                  45 aat gaa ttc caa aga cat gtg gaa gaa tat gaa gta tca ctt att cta   192
Asn Glu Phe Gln Arg His Val Glu Glu Tyr Glu Val Ser Leu Ile Leu
         50                  55                  60 cag ctt tgt aaa att cca cta aaa gct gag gtg cta gca cag att aat   240
Gln Leu Cys Lys Ile Pro Leu Lys Ala Glu Val Leu Ala Gln Ile Asn
 65                  70                  75                  80 gca atg aac tct gac att ttg gaa agt tgg cag tta ggt ttt gta cct   288
Ala Met Asn Ser Asp Ile Leu Glu Ser Trp Gln Leu Gly Phe Val Pro
                 85                  90                  95 aca cca gat aat cct atc cac gac aca tac aga tac tta gat tca ttg   336
Thr Pro Asp Asn Pro Ile His Asp Thr Tyr Arg Tyr Leu Asp Ser Leu
             100                 105                 110 gct acc cgc tgc cca gaa aaa gtg cct gca aag gaa aag gag gac cct   384
Ala Thr Arg Cys Pro Glu Lys Val Pro Ala Lys Glu Lys Glu Asp Pro
         115                 120                 125 tat gct aag tat gta ttt tgg aat gtt gat ttg tct gaa cgt tta tct   432
Tyr Ala Lys Tyr Val Phe Trp Asn Val Asp Leu Ser Glu Arg Leu Ser
     130                 135                 140 ttg gat ttg gac caa ttt cct tta gga cga aaa tt                    467
Leu Asp Leu Asp Gln Phe Pro Leu Gly Arg Lys
145                 150                 155
```

```
<210> SEQ ID NO 14
<211> LENGTH: 155
<212> TYPE: PRT
<213> ORGANISM: Papilloma virus capsid

<400> SEQUENCE: 14

Gln Gly His Asn Asn Gly Ile Leu Trp Gly Asn Gln Leu Phe Val Thr
 1               5                  10                  15

Val Leu Asp Asn Thr Arg Asn Thr Asn Phe Ser Ile Ala Val Tyr Gln
            20                  25                  30

Glu Gln Lys Lys Val Lys Glu Ile Gln Ser Tyr Asp Ser Thr Lys Phe
        35                  40                  45

Asn Glu Phe Gln Arg His Val Glu Glu Tyr Glu Val Ser Leu Ile Leu
    50                  55                  60

Gln Leu Cys Lys Ile Pro Leu Lys Ala Glu Val Leu Ala Gln Ile Asn
65                  70                  75                  80

Ala Met Asn Ser Asp Ile Leu Glu Ser Trp Gln Leu Gly Phe Val Pro
                85                  90                  95

Thr Pro Asp Asn Pro Ile His Asp Thr Tyr Arg Tyr Leu Asp Ser Leu
            100                 105                 110

Ala Thr Arg Cys Pro Glu Lys Val Pro Ala Lys Glu Lys Glu Asp Pro
        115                 120                 125

Tyr Ala Lys Tyr Val Phe Trp Asn Val Asp Leu Ser Glu Arg Leu Ser
    130                 135                 140

Leu Asp Leu Asp Gln Phe Pro Leu Gly Arg Lys
145                 150                 155

<210> SEQ ID NO 15
<211> LENGTH: 467
<212> TYPE: DNA
<213> ORGANISM: Papilloma virus capsid
<220> FEATURE:
<221> NAME/KEY: CDS
<222> LOCATION: (1)..(465)
<223> OTHER INFORMATION:

<400> SEQUENCE: 15 caa ggt cac aat aat ggt att ctg tgg gct aat gaa atg ttt gtc act      48
Gln Gly His Asn Asn Gly Ile Leu Trp Ala Asn Glu Met Phe Val Thr
 1               5                  10                  15 gtt gta gac aac aca cga aat act aat ttc agt ata tcc atg tat aca      96
Val Val Asp Asn Thr Arg Asn Thr Asn Phe Ser Ile Ser Met Tyr Thr
            20                  25                  30 gaa gct ggg gag ata aaa aat ata gcc aac tac gat gcc aaa aaa ttt     144
Glu Ala Gly Glu Ile Lys Asn Ile Ala Asn Tyr Asp Ala Lys Lys Phe
        35                  40                  45 agg gag tat tta aga cac gtg gaa gag tat gaa att tct cta att tca     192
Arg Glu Tyr Leu Arg His Val Glu Glu Tyr Glu Ile Ser Leu Ile Ser
    50                  55                  60 caa ctt tgt aaa ata cct ctg aag gca gag gtc ctt gca caa ata aat     240
Gln Leu Cys Lys Ile Pro Leu Lys Ala Glu Val Leu Ala Gln Ile Asn
65                  70                  75                  80 gca atg aat tcc tct tta ttg gag gac tgg caa ctg ggg ttt gtg cct     288
Ala Met Asn Ser Ser Leu Leu Glu Asp Trp Gln Leu Gly Phe Val Pro
                85                  90                  95 acc cct gat aat ccc ata caa gac act tat aga tat att gat tcc tta     336
Thr Pro Asp Asn Pro Ile Gln Asp Thr Tyr Arg Tyr Ile Asp Ser Leu
            100                 105                 110 gcc aca cgt tgt cct gac aaa aat cct cca aag gaa aaa gaa gat ccc     384
Ala Thr Arg Cys Pro Asp Lys Asn Pro Pro Lys Glu Lys Glu Asp Pro
```

```
tat aaa aat tta act ttt tgg act gta gat ctt act gag cga ctt tcc      432
Tyr Lys Asn Leu Thr Phe Trp Thr Val Asp Leu Thr Glu Arg Leu Ser
        130                 135                 140 ttg gag ttg gat caa tat cct ctg gga cga aag tt                       467
Leu Glu Leu Asp Gln Tyr Pro Leu Gly Arg Lys
145                 150                 155
```

<210> SEQ ID NO 16
<211> LENGTH: 155
<212> TYPE: PRT
<213> ORGANISM: Papilloma virus capsid

<400> SEQUENCE: 16

```
Gln Gly His Asn Asn Gly Ile Leu Trp Ala Asn Glu Met Phe Val Thr
1               5                   10                  15

Val Val Asp Asn Thr Arg Asn Thr Asn Phe Ser Ile Ser Met Tyr Thr
            20                  25                  30

Glu Ala Gly Glu Ile Lys Asn Ile Ala Asn Tyr Asp Ala Lys Lys Phe
        35                  40                  45

Arg Glu Tyr Leu Arg His Val Glu Glu Tyr Glu Ile Ser Leu Ile Ser
    50                  55                  60

Gln Leu Cys Lys Ile Pro Leu Lys Ala Glu Val Leu Ala Gln Ile Asn
65                  70                  75                  80

Ala Met Asn Ser Ser Leu Leu Glu Asp Trp Gln Leu Gly Phe Val Pro
                85                  90                  95

Thr Pro Asp Asn Pro Ile Gln Asp Thr Tyr Arg Tyr Ile Asp Ser Leu
            100                 105                 110

Ala Thr Arg Cys Pro Asp Lys Asn Pro Pro Lys Glu Lys Glu Asp Pro
        115                 120                 125

Tyr Lys Asn Leu Thr Phe Trp Thr Val Asp Leu Thr Glu Arg Leu Ser
    130                 135                 140

Leu Glu Leu Asp Gln Tyr Pro Leu Gly Arg Lys
145                 150                 155
```

<210> SEQ ID NO 17
<211> LENGTH: 389
<212> TYPE: DNA
<213> ORGANISM: Papilloma virus capsid
<220> FEATURE:
<221> NAME/KEY: CDS
<222> LOCATION: (1)..(387)
<223> OTHER INFORMATION:

<400> SEQUENCE: 17

```
aat caa atg ttt att aca gtg gta gac aac aca cga aac acc aat ttc      48
Asn Gln Met Phe Ile Thr Val Val Asp Asn Thr Arg Asn Thr Asn Phe
1               5                   10                  15 agt att tca gtt tat agt gaa ggt gga caa ata aaa gat atc agg gac      96
Ser Ile Ser Val Tyr Ser Glu Gly Gly Gln Ile Lys Asp Ile Arg Asp
            20                  25                  30 tac aca tct aca cag ttc agg gaa tat tta agg cat gtg gag gaa tat     144
Tyr Thr Ser Thr Gln Phe Arg Glu Tyr Leu Arg His Val Glu Glu Tyr
        35                  40                  45 gaa ata tct gtc ata ttg cag tta tgt aaa ata cct tta aaa gca gaa     192
Glu Ile Ser Val Ile Leu Gln Leu Cys Lys Ile Pro Leu Lys Ala Glu
    50                  55                  60 gtc ttg gct caa ata aat gcc atg aac ccc tta tta ttg gag gac tgg     240
Val Leu Ala Gln Ile Asn Ala Met Asn Pro Leu Leu Leu Glu Asp Trp
65                  70                  75                  80
```

```
caa tta gga ttt gtc cct aca cct gac aat cca att cat gat acc tac      288
Gln Leu Gly Phe Val Pro Thr Pro Asp Asn Pro Ile His Asp Thr Tyr
                85                  90                  95 aga ttt att gac tct ttg gct atc cga tgc cct gac aaa aat ccc cca      336
Arg Phe Ile Asp Ser Leu Ala Ile Arg Cys Pro Asp Lys Asn Pro Pro
                100                 105                 110 aaa gaa aaa cct gac cct tat gaa ggc tta aac ttt tgg aat gtt gat      384
Lys Glu Lys Pro Asp Pro Tyr Glu Gly Leu Asn Phe Trp Asn Val Asp
            115                 120                 125 cta tc                                                               389
Leu
```

<210> SEQ ID NO 18
<211> LENGTH: 129
<212> TYPE: PRT
<213> ORGANISM: Papilloma virus capsid

<400> SEQUENCE: 18

```
Asn Gln Met Phe Ile Thr Val Val Asp Asn Thr Arg Asn Thr Asn Phe
1               5                   10                  15

Ser Ile Ser Val Tyr Ser Glu Gly Gly Gln Ile Lys Asp Ile Arg Asp
                20                  25                  30

Tyr Thr Ser Thr Gln Phe Arg Glu Tyr Leu Arg His Val Glu Glu Tyr
            35                  40                  45

Glu Ile Ser Val Ile Leu Gln Leu Cys Lys Ile Pro Leu Lys Ala Glu
    50                  55                  60

Val Leu Ala Gln Ile Asn Ala Met Asn Pro Leu Leu Leu Glu Asp Trp
65                  70                  75                  80

Gln Leu Gly Phe Val Pro Thr Pro Asp Asn Pro Ile His Asp Thr Tyr
                85                  90                  95

Arg Phe Ile Asp Ser Leu Ala Ile Arg Cys Pro Asp Lys Asn Pro Pro
                100                 105                 110

Lys Glu Lys Pro Asp Pro Tyr Glu Gly Leu Asn Phe Trp Asn Val Asp
            115                 120                 125

Leu
```